(12) United States Patent
Borgenicht

(10) Patent No.: US 6,405,082 B1
(45) Date of Patent: Jun. 11, 2002

(54) METHOD AND APPARATUS FOR DISTINGUISHING BETWEEN THERAPY MODES IN A DEFIBRILLATOR

(75) Inventor: Fred H. Borgenicht, Dover, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/490,253

(22) Filed: Jan. 24, 2000

(51) Int. Cl.[7] .................................................. A61N 1/39
(52) U.S. Cl. ............................................................. 607/5
(58) Field of Search ..................... 607/5, 7, 4

(56) References Cited

U.S. PATENT DOCUMENTS

| | | | | |
|---|---|---|---|---|
| 5,720,770 A | * | 2/1998 | Nappholz et al. | |
| 5,792,190 A | * | 8/1998 | Olson et al. | |
| 6,064,909 A | * | 5/2000 | Barkley et al. | |

* cited by examiner

Primary Examiner—Jeffrey R. Jastrzab

(57) ABSTRACT

A defibrillator capable of delivering a plurality of therapies to a patient wherein the defibrillator emits an audible prompt to the user identifying the selected therapy mode. The prompt is delivered when either the capacitor is charging, or the capacitor is charged, or the therapy is delivered.

18 Claims, 4 Drawing Sheets

METHOD AND APPARATUS FOR DISTINGUISHING BETWEEN THERAPY MODES IN A DEFIBRILLATOR

FIELD OF THE INVENTION

The present invention relates in general to defibrillators and defibrillator trainers, particularly defibrillators capable of delivering multiple therapies to a patient. More specifically, the invention relates to defibrillators capable of delivering asynchronous and synchronous defibrillation therapy. The defibrillators of the invention are manual defibrillators, but could also include automatic or semi-automatic external defibrillators (AEDs) provided it is capable of delivering multiple therapies or at least synchronous and asynchronous defibrillation therapy. In particular, this invention relates to a method for distinguishing between asynchronous and synchronous therapy modes in a defibrillator as well as a defibrillator that operates according to the method.

BACKGROUND OF THE INVENTION

Sudden cardiac death is the leading cause of death in the United States, with one person dying every two minutes. Most sudden cardiac death is caused by ventricular fibrillation ("VF"), in which the heart's muscle fibers contract without coordination, thereby interrupting normal blood flow to the body. When VF occurs, the patient loses consciousness as a result of the interruption in blood flow. The only known effective treatment for VF is electrical defibrillation, in which an electrical pulse is applied to the patient's heart. The electrical pulse must be delivered within a short time after onset of VF in order for the patient to have any reasonable chance of survival. Electrical defibrillation may also be used to treat shockable ventricular tachycardia ("VT"). Accordingly, defibrillation is the appropriate therapy for any shockable rhythm, i.e., VF or shockable VT. In delivering defibrillation therapy to treat VF or shockable VT, because the cardiac rhythm is disorganized, delivery of therapy is not synchronized to the cardiac rhythm.

Atrial fibrillation ("AF") is a commonly occurring cardiac arrhythmia. During AF the atria of the heart is in fibrillation, but the ventricles continue to pump properly. Although the patient is conscious, AF is still a significant health risk because, if left untreated, AF can result in stroke. AF is treated by delivering a synchronized defibrillation energy pulse to the patient. The energy pulse is synchronized with the R wave of the QRS complex of the electrocardiogram ("ECG") of the heart, where the QRS complex represents activation of the ventricles. Failure to deliver the energy at the appropriate time during the QRS complex could result in VF. Further information on treatment of Cardiac Arrhythmias can be obtained in Emergency Cardiac Care Committee, et al., "III. Adult Advanced Cardiac Life Support" JAMA 268:2172–2183 (1992). See also, Marriott's Practical Electrocardiography, 9$^{th}$ Ed. (Galen Wagner).

Because of these two different therapy modes, defibrillators typically include a mode for delivering therapy to treat VF (using an unsynchronized defibrillation energy), and to treat AF (using a synchronized defibrillation energy also referred to as "synchronized cardioversion"). Additionally, these devices may also be capable of pacing and monitoring. Importantly, when treating a cardiac emergency, a caregiver must not deliver a synchronized shock when an unsynchronized shock is required or vise versa. If a synchronized shock is attempted to treat VF, no therapy will be delivered since the cardiac signal is chaotic and the defibrillator will not detect an R-wave from which to synchronize delivery of the energy pulse. Conversely, if an unsynchronized shock is delivered to a patient suffering from AF, the patient will likely go into VF, thus causing a serious.

One drawback to currently available defibrillators capable of delivering multiple therapies, such as synchronized and unsynchronized shocks, is that the caregiver must look at the device to determine the current treatment mode. For safety reasons, the device is checked before each use as well as during use. Further, once therapy has begun there is no way for the caregiver to confirm the correct treatment mode without returning to the device settings.

What is needed, therefore, is a way for the defibrillator to automatically provide confirmation of the treatment mode to the user when the device is in use without requiring the user to review the device settings.

SUMMARY OF THE INVENTION

A method of advising a user of a current therapy mode setting of a defibrillator comprising: deploying the defibrillator, the defibrillator having a controller, an energy delivery system operable by the controller to deliver an electrical shock from an energy source to an electrode interface, and an audible prompt generator, wherein the defibrillator is attached to a patient; detecting input from the user; delivering an audible prompt to the user confirming the current therapy mode setting of the defibrillator; and delivering therapy to a patient in the selected therapy mode. The step of delivering a prompt to the user can be performed when the defibrillator is charging the energy source, when the energy source is charged, when the defibrillator delivering therapy to the patient, or at a plurality of times. These prompts can be tonal prompts or verbal prompts. Tonal prompts typically would be either high frequency tones or low frequency tones.

An external defibrillator comprising: a controller, an energy delivery system operable by the controller to deliver an electrical shock from an energy source to an electrode interface in a plurality of treatment modes; and an audible prompt generator to deliver an audible prompt indicative of a current therapy mode to the user. The audible prompt generator generates tonal prompts or verbal prompts. Tonal prompts can be either high frequency tones or low frequency tones. The prompts are delivered by the defibrillator to the user when the defibrillator is charging the energy source, when the energy source is charged, when the defibrillator delivering therapy to the patient, or at a plurality of times.

Thus, it is an object of the present invention to provide medical personnel and caregivers with a defibrillator that automatically confirms the operation mode of the device during therapy.

It is a further object of the invention to provide a defibrillator that generates an audible prompt to the user of the operation mode. This audible prompt may be either tonal or verbal and may occur during charge, at charge done or at shock delivery.

DETAILED DESCRIPTION OF THE INVENTION

The following discussion is presented to enable a person skilled in the art to make and use the invention. The discussion is directed to a manual defibrillator, but, as will be appreciated by those of skill in the art, aspects of the invention could be applied towards AEDs without departing from the scope of the invention. Various modifications to the preferred embodiment will be readily apparent to those skilled in the art, and the generic principles defined herein may be applied to other embodiments and applications without departing from the spirit and scope of the present invention as defined by the appended claims. Thus, the present invention is not intended to be limited to the embodiment shown, but is to be accorded the widest scope consistent with the principles and features disclosed herein.

Figure 1:
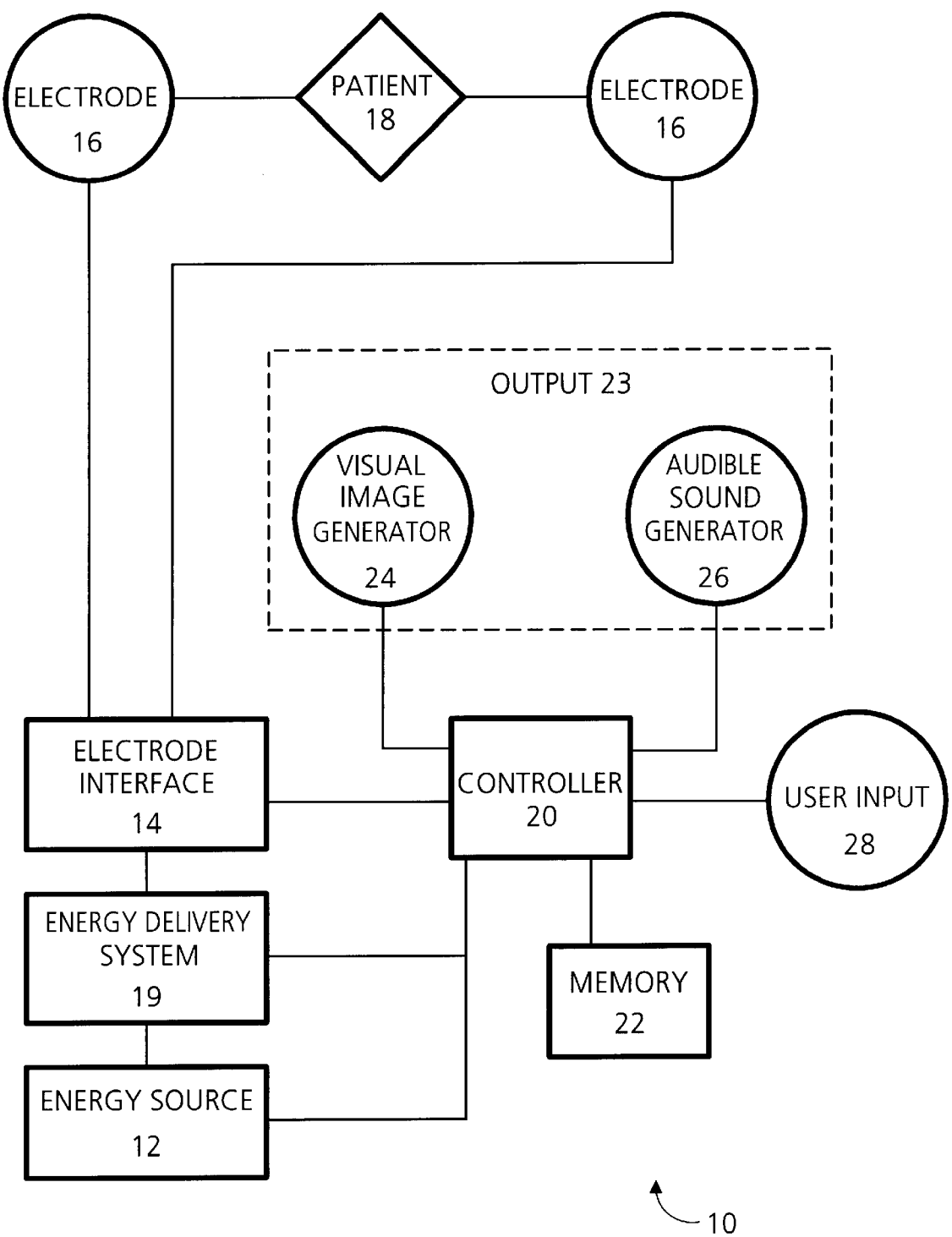
FIG. 1 is a block diagram of an electrotherapy device that might be suitable to employ the methods of the present invention.

FIG. 1 is a schematic block diagram of a defibrillator system 10 according to a preferred embodiment of this invention. The defibrillator system 10 comprises an energy source 12 to provide voltage or current pulses. A controller 20 operates an energy delivery system 19 to selectively connect and disconnect energy source 12 to and from a pair of electrodes 16 electrically attached to a patient 18 through an electrode interface 14. When the energy delivery system 19 is connected to the electrodes 16 electrotherapy is delivered to the patient. The defibrillator system 10 is an electrotherapy device such as a manual defibrillator or AED. The defibrillator or AED is capable of at least two therapy modes. In a preferred embodiment, the defibrillator or AED is capable of: synchronous cardioversion and asynchronous defibrillation therapy. Alternatively, defibrillator system 10 may be a defibrillator trainer that simulates the behavior of a manual defibrillator or AED in use, in which case the electrode interface and energy delivery system may be omitted.

Memory 22 records data collected by the defibrillator while monitoring and treating a patient. Memory 22 may include any appropriate memory device such as FLASH, EEPROM, ROM or RAM. Memory 22 may be removable or, alternatively, may be integral with the defibrillator. Removable memory could include a PCMCIA card or a compact flash card (such as those available from M-Systems).

Visual image generator 24 displays, among other things, current ECG and treatment mode. The visual image generator 24 may be, for example, a liquid crystal display ("LCD") or a cathode ray tube ("CRT") display. Additionally, an audible sound generator 26 is provided. Activation of the visual image generator 24 and the audible sound generator 26 is controlled by the controller 20.

In a preferred embodiment, user input 28 is provided to, for example, enable the user to change treatment modes or to deliver therapy to a patient. Typically in a manual defibrillator one or more user inputs is provided to enable the user to change treatment modes of the device. User inputs include dedicated buttons for activation of a feature (such as "on/off" or "shock" buttons), soft keys for activation of a feature (where one button changes functionality depending on the operation mode of the device), and QWERTY keyboards, to name a few.

The electrotherapy device operating modes can include patient treatment (in which, e.g., a therapeutic pulse is delivered to a patient via energy delivery system 19), monitoring (in which, e.g., the patient's bioparameters are monitored, bioparameters include for example patient ECG), incident review function (wherein the device pauses the monitoring and treatment function in order to enable a user to review treatment history for a patient), and self-test mode (in which device 10 runs self-test procedures to determine its operating condition).

Figure 2:
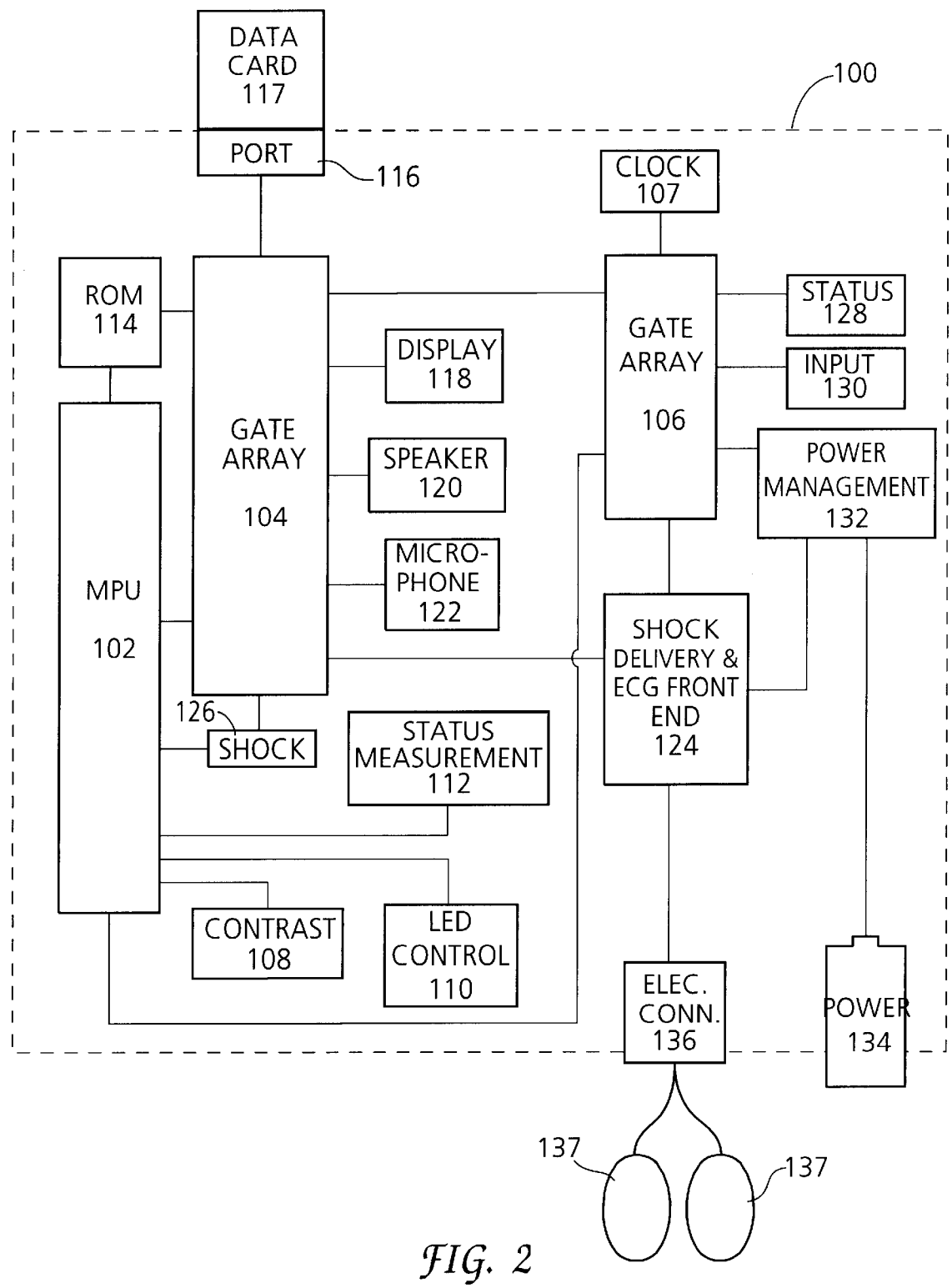
FIG. 2 is a more detailed block diagram of the major components of an electrotherapy device.

The major components of an external defibrillator according to a preferred embodiment are shown in FIG. 2 in block diagram form. Defibrillator control functions are divided among a microprocessor unit ("MPU") 102 and two gate arrays 104 and 106. It should be understood, however, that gate arrays 104 and 106 are optional, and their functions can be performed by other circuits.

MPU 102 performs program steps according to software instructions provided to it from ROM 114. MPU 102 controls the operation of certain buttons and certain system light emitting diodes ("LED's") 110 (such as, for example, LED's associated with the shock button or a charge done button). MPU 102 also receives system status information as shown by block 112.

Gate array 104 implements the memory map to system ROM 114, data card port 116 and other system memory elements. System ROM 114 is preferably flash ROM, although EPROM or any other electrically erasable and programmable nonvolatile memory could be used. Where a data card port 116 is provided as a means to enable patient data to be removed from the defibrillator, it is preferable that a data card slot configured to interface with PC data cards conforming to the 1995 PC Card standard be provided.

Gate array 106 receives time information from clock 107. Gate array 106 may also provide a system monitor function by performing self-tests of the defibrillator and its components. The gate array 106 displays the operational status of the defibrillator on a status display 128. Gate array 106 is also the defibrillator's interface with user input 130. User input includes, for example, on/off, shock, operation mode selection, QWERTY keyboards, soft keys, energy selections, etc.

Gate array 106 controls the power management subsystem 132 to provide power to operate system components from power module 134 and to provide energy to the shock delivery system's capacitor(s) for a therapeutic shock during treatment mode. The power module 134 may be any appropriate source of power to operate the defibrillator. Power module 134 may be, for example, an AC power source, chargeable batteries or rechargeable batteries. Gate array 106 may also interface with the defibrillator's ECG front end 124. In that case, gate array 106 enables the shock delivery system to deliver a shock in response to detection of a patient ECG pattern requiring treatment (and actuation of the shock button), and controls delivery of the shock to electrode connector 136 in response to shock delivery status information obtained during delivery of the shock. Further information regarding this last function may be found in U.S. Pat. No. 5,735,879 to Gliner et al. for "Electrotherapy Method for External Defibrillators;" U.S. Pat. No. 5,607,454 to Cameron et al. for "Electrotherapy Method and Apparatus;" and U.S. Pat. No. 4,840,177 to Charbonnier, et al. For "Current-Based Defibrillator," the disclosures of which are incorporated herein by reference.

These defibrillator components communicate with each other over suitable communication buses.

During patient treatment and monitoring mode, the defibrillator receives ECG information from a patient through electrodes 137. In a manual defibrillator, the user analyses the ECG data, makes a decision as to appropriate therapy, selects a therapy mode (e.g., synchronized or asynchronized defibrillation or pacing). Once the therapy mode has been selected, the user delivers the therapy to the patient by actuating an input 128. When treating VF with a manual defibrillator, activation of user input will result in defibrillation energy being delivered to the patient. When treating AF with a manual defibrillator, delivery of defibrillation energy will be delayed, if appropriate, in order to synchronize the delivery with the QRS complex.

In an AED the defibrillator analyzes the rhythm and determines the appropriate therapy. Where the AED is semi-automatic, a shock is delivered to the patient through the electrodes if a shock is advised and if a shock button is actuated by a user. As previously described, in treating VF, delivery of energy is not synchronized prior to delivery to the patient; in treating AF, delivery of energy is synchronized to the QRS complex prior to delivery to the patient. In a fully automatic AED, a shock would be delivered to the patient without further user intervention.

Figure 3:
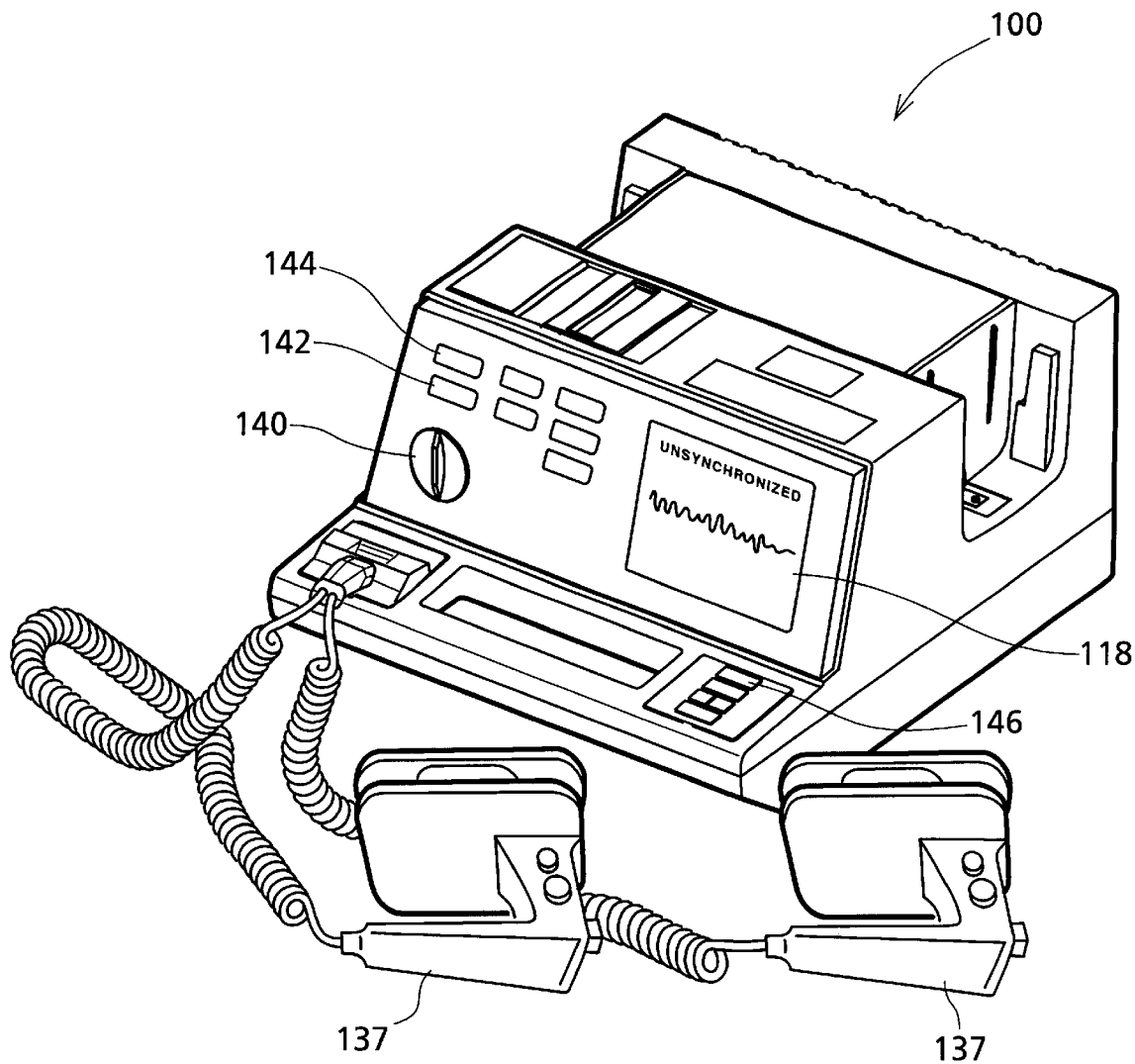
FIG. 3 is a top elevational view of an electrotherapy device with a display screen that illustrates the operational mode of the device and user activation buttons for selecting the operation mode of the device.

FIG. 3 illustrates a defibrillator 100 according to the invention. An ECG is shown on display 118. A legend also appears on the display 118, in this case along the top, indicating the current device treatment mode. An input for energy selection 140 may be provided to enable the user to select a therapy energy level (e.g. 200 J). An input for charging the defibrillator to deliver an unsynchronized shock 144 may be provided along with an input for delivering a synchronized shock 142. Additional inputs may be provided for monitoring, pacing functions, and recording functions. However, these inputs are not described in order to avoid obscuring the invention.

Figure 4:
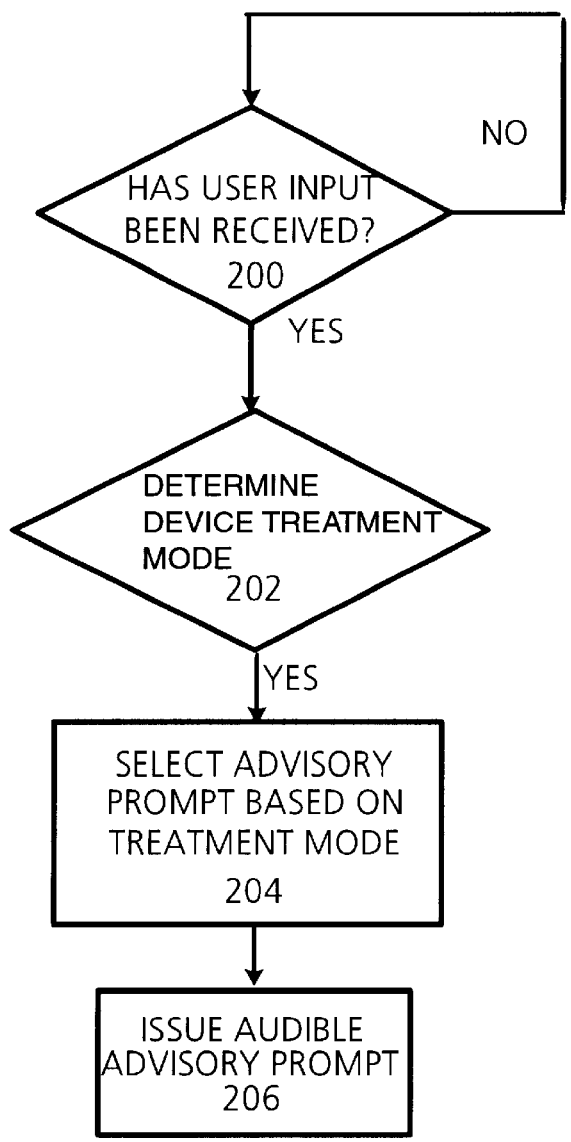
FIG. 4 is a flow chart demonstrating the operation of an electrotherapy device that automatically communicates therapy mode to the caregiver.

FIG. 4 is a flow chart that demonstrates an example of operation of the defibrillator 100 according to the invention. As shown by block 200, the defibrillator 100 determines whether the user has actuated the device. If not, the audible prompt mechanism continues in standby mode. Otherwise, if actuation has been received (typically from the user), the defibrillator determines the current treatment mode 202. As discussed above, treatment mode includes at least asynchronous and synchronous defibrillation. Other treatment modes may be included as appropriate for the operation of the device. Based on the identified treatment mode, the defibrillator selects an audible prompt 204. Audible prompts may be either tonal or verbal. In one embodiment, different tones are used to distinguish between the therapy modes. In this embodiment, tones can be differentiated by the duty cycle of the tone where the frequency is kept constant. In that case, one series of tones is delivered at a rate of 1 beep per second (duty cycling on for 0.5 second and off for 0.5 second) and the other tone is delivered at a rate of 2 beeps per second (duty cycling on for 0.25 second and off for 0.25 second). As will be appreciated by those of skill in the art, the type of audible tone associated with the therapy mode is unimportant as long as the tones are audibly distinguishable by the user. For example, instead of varying duty cycle, the frequency of the tone could be varied or a plurality of frequencies could be used to generate an identifiable prompt. Other combinations and permutations of variations would be apparent to those of skill in the art in order to maximize the user's ability to distinguish between the therapy modes.

In an alternate embodiment, the prompts are verbal. In this case, an appropriate verbal prompt may be, for example, "charging to deliver unsynchronized energy pulse for VF."

Following selection of the audible prompt, the defibrillator delivers the prompt 206. Delivery of the prompt may occur while the defibrillator is charging the capacitor prior to delivery of patient therapy. Alternatively, the prompt may be issued after the capacitor has been charged and prior to delivery of the therapy to the patient. Finally, the prompt may be delivered concurrently with delivery of therapy. It is also within the scope of the invention that a plurality of prompts be delivered. Thus, the prompt may be issued at one or more of the phases discussed above.

The main object of this invention is to reduce the amount of time a caregiver spends visually confirming the operational settings of the defibrillator in order to reduce the amount of time before delivery of therapy to the patient without compromising patient safety. Thus, where it is anticipated that the caregiver may have difficulty hearing the advisory prompts or distinguishing between the two prompts, a visual indicator may be provided in addition to or in place of the audible prompts. Such visual indicator might be, for example, a light which pulses a two different frequencies or a light that changes colors depending on the mode selected (e.g., red for asynchronous energy and yellow for synchronous energy). Preferably, where a visual indicator is used, it will be such that it can quickly and easily be discerned without difficulty and without requiring inspection of the device settings.

It should be appreciated that the scope of the invention is not limited to the embodiments described above. Various modifications and alterations might be made by those of skill in the art without departing from the scope and spirit of the present invention.

What is claimed is:

1. A method of advising a user of a current therapy mode setting of a defibrillator comprising:
   a. deploying the defibrillator, the defibrillator having a controller, an energy delivery system operable by the controller to deliver an electrical shock from an energy source to an electrode interface, and an audible prompt generator, wherein the defibrillator is attached to a patient;
   b. detecting input from the user;
   c. delivering an audible prompt to the user confirming the current therapy mode setting of the defibrillator; and
   d. delivering therapy to a patient in the selected therapy mode.

2. The method of claim 1 wherein the step of delivering a prompt to the user is performed when the defibrillator is charging the energy source.

3. The method of claim 1 wherein the step of delivering a prompt to the user is performed when the energy source is charged.

4. The method of claim 1 wherein the step of delivering a prompt to the user is performed when the defibrillator is delivering therapy to the patient.

5. The method of claim 1 wherein the prompt delivered is a tonal prompt.

6. The method of claim 5 wherein the tonal prompt is a high frequency tone.

7. The method of claim 5 wherein the tonal prompt is a low frequency tone.

8. The method of claim 1 wherein the step of delivering a prompt to the user is performed at a plurality of times prior to delivery of therapy to the patient.

9. The method of claim 1 wherein the prompt is verbal.

10. An external defibrillator comprising:
    a controller, an energy delivery system operable by the controller to deliver an electrical shock from an energy source to an electrode interface in a plurality of treatment modes; and an audible prompt generator to deliver an audible prompt indicative of a current therapy mode to the user.

11. The defibrillator of claim 10 wherein the audible prompt generator generates a tonal prompt.

12. The defibrillator of claim 11 wherein the audible prompt generator generates a high frequency tone.

13. The defibrillator of claim 11 wherein the audible prompt generator generates a low frequency tone.

14. The defibrillator of claim 10 wherein the audible prompt generator generates a verbal prompt.

15. The defibrillator of claim 10 wherein the audible prompt generator generates the prompt when the defibrillator is charging the energy source.

16. The defibrillator of claim 10 wherein the audible prompt generator generates the prompt when the defibrillator has charged the energy source.

17. The defibrillator of claim 10 wherein the audible prompt generator generates the prompt when the defibrillator is delivering therapy.

18. The defibrillator of claim 10 wherein the audible prompt generator generates the prompt at a plurality of times during delivery of a therapy.

* * * * *